US00PP33838P2

(12) United States Plant Patent
Royakkers

(10) Patent No.: US PP33,838 P2
(45) Date of Patent: Jan. 11, 2022

(54) BLACKBERRY PLANT NAMED 'JANDRIE'

(50) Latin Name: ***Rubus* L. subgenus *Rubus***
Varietal Denomination: Jandrie

(71) Applicant: ROYAKKERS EXPLORE BVBA, Kinrooi (BE)

(72) Inventor: Jan Royakkers, Kinrooi (BE)

(73) Assignee: ROYAKKERS EXPLORE BVBA, Kinrooi (BE)

( * ) Notice: Subject to any disclaimer, the term of this patent is extended or adjusted under 35 U.S.C. 154(b) by 0 days.

(21) Appl. No.: 17/232,011

(22) Filed: Apr. 15, 2021

(51) Int. Cl.
*A01H 6/74* (2018.01)
*A01H 5/02* (2018.01)

(52) U.S. Cl.
USPC ..... Plt./203

(58) Field of Classification Search
USPC ..... Plt./203
See application file for complete search history.

(56) References Cited

U.S. PATENT DOCUMENTS

PP6,782 P 5/1989 Jennings
PP25,502 P3 5/2015 Sills

OTHER PUBLICATIONS

PLUTO Plant Variety Database Jul. 17, 2021. p. 1.*

* cited by examiner

*Primary Examiner* — Annette H Para
(74) *Attorney, Agent, or Firm* — Panitch Schwarze Belisario & Nadel LLP; Stephany G. Small

(57) ABSTRACT

A new and distinct variety of blackberry plant variety, referred to by its cultivar name, 'Jandrie', is disclosed. The new variety forms large fruits which are firm and very sweet. The fruit production begins early, and the harvest interval is long, which results in a high yield. The postharvest handling is excellent.

11 Drawing Sheets

Latin name of the genus and species:
Family: Rosaceae.
Genus and species: *Rubus* L. subgenus *Rubus*.
Variety denomination:
Variety denomination: 'Jandrie'.

CROSS REFERENCE TO RELATED APPLICATIONS

None.

STATEMENT REGARDING FEDERALLY-SPONSORED RESEARCH AND DEVELOPMENT

None.

BACKGROUND OF THE NEW PLANT

The present invention relates to a new and distinct cultivar of blackberry (botanically known as *Rubus* L. subgenus *Rubus*) plant, referred to as 'Jandrie', as herein described and illustrated. The new blackberry plant variety 'Jandrie' is a commercial variety intended for the fresh fruit market. 'Jandrie' was selected for its high yields of fruit, large sized fruit, and sweet taste of the fruit.

The new blackberry plant originated in Kinrooi, Belgium, in May 2016 and was produced from seed taken from a commercially available fruit of unknown origin. The female parent and the male parent of 'Jandrie' are unknown. Selective study of two-years-old seedlings resulted in the identification of a single plant of the new variety. The selection was made based on the sweet taste of the fruit of the seedling which was, at that time, quite small. The original seedling was first divided to obtain two plants in 2017. Stem cuttings from the two plants were taken and these cuttings produced plants forming a primocane in 2018 and a floricane in 2019. The exceptional quality of the fruit was discovered in 2019, which are a very large size but nevertheless retain its initially discovered sweet taste. The plants also have a high yield.

The new variety has been found to undergo asexual reproduction by stem cuttings forming a primocane in 2018 and a floricane in 2019 in Kinrooi, Belgium. Also, in 2018 and in 2019 the new variety was asexually propagated by tissue culture in Heerhugowaard, The Netherlands and were further grown in Kinrooi, Belgium. The tissue cultured asexually propagated new variety plants produced fruit in 2020. Asexual propagation by tissue culture in Heerhugowaard, The Netherlands and Kinrooi, Belgium and by stem cuttings in Kinrooi, Belgium has shown that the characteristics of the new variety are stable and strictly transmissible by such asexual propagation from one generation to another. Accordingly, the new variety undergoes asexual propagation in a true-to-type manner.

Plant Breeders' Right Application Number 2018/1631 was filed at Community Plant Variety Office in the European Union on Jun. 28, 2018 for the new variety. The new variety was not sold, offered for sale, or otherwise available to the public more than one year before the filing of the instant application.

SUMMARY OF THE INVENTION

The new blueberry plant variety 'Jandrie' has not been observed under all possible environmental conditions. The phenotype may vary somewhat with variations in environment and cultural practices such as temperature and light intensity without, however, any variance in genotype.

It was found that the new variety of blackberry plant of the present invention possesses the following combination of characteristics when grown under normal horticulture practices, in Kinrooi, Belgium, in a greenhouse which maintains a minimum temperature of 16° C. during the day, or 20° C. under sunny conditions, and 8° C. during the night:

1. High yields, of 65 tons/ha or even higher under optimal conditions;
2. Large fruits of even up to 17 to 18 g/fruit;
3. Early variety; and
4. Very sweet taste, in particular due to a limited amount of acids in the ripe fruit.

BRIEF DESCRIPTION OF THE DRAWINGS

The accompanying photographic illustration shows typical specimens in full color of the foliage and fruit of the new variety 'Jandrie'. The colors are as nearly true as is reasonably possible in a color representation of this type. The photographs are of in vitro propagated two-years-old plants growing in a greenhouse and of fruit thereof (fruiting for the first year).

DETAILED BOTANICAL DESCRIPTION

Figure 1:
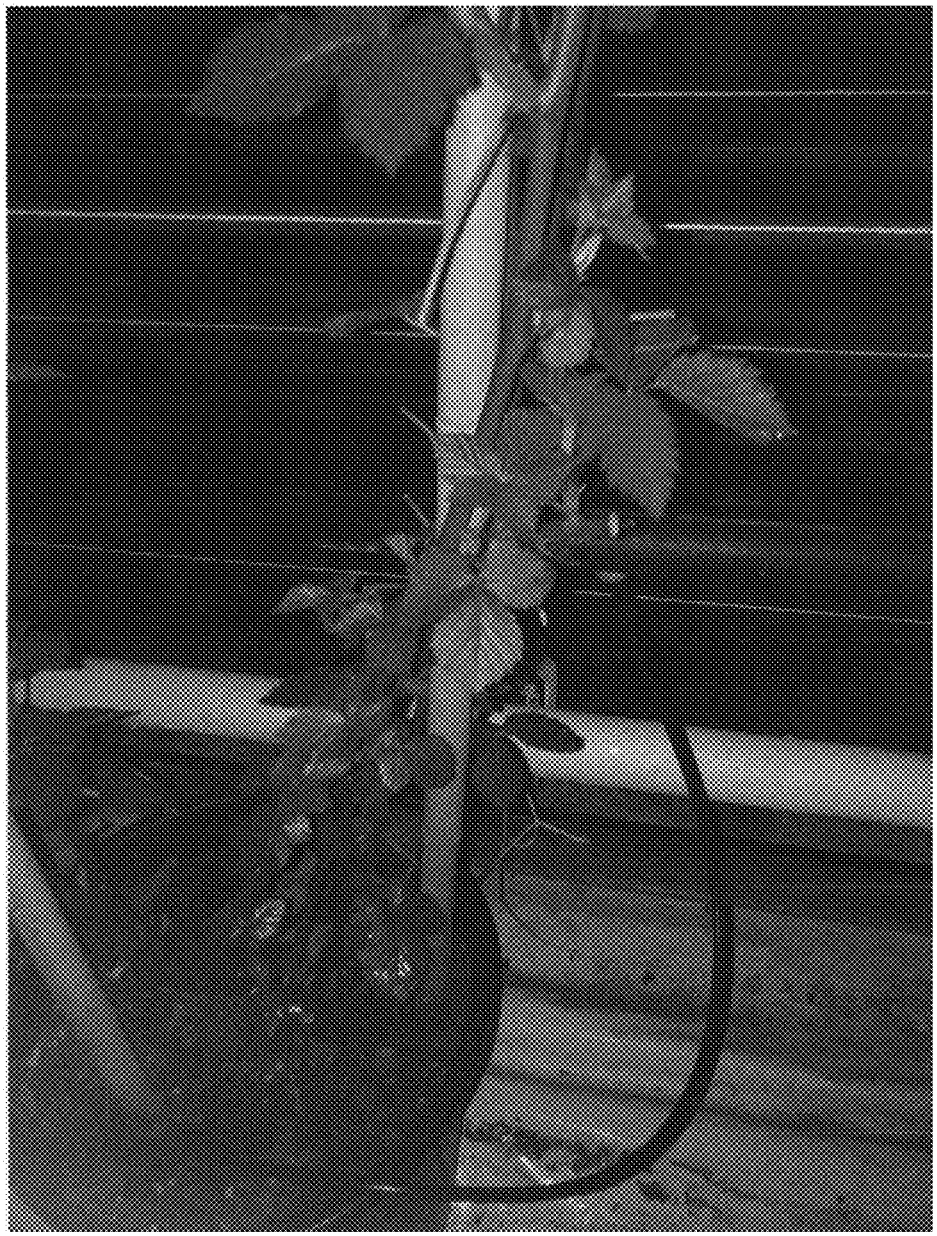
FIG. 1 is a photograph of the new variety 'Jandrie', demonstrating the plant's leaves and growth habit. The specimen was photographed February 2021.
Figure 2:
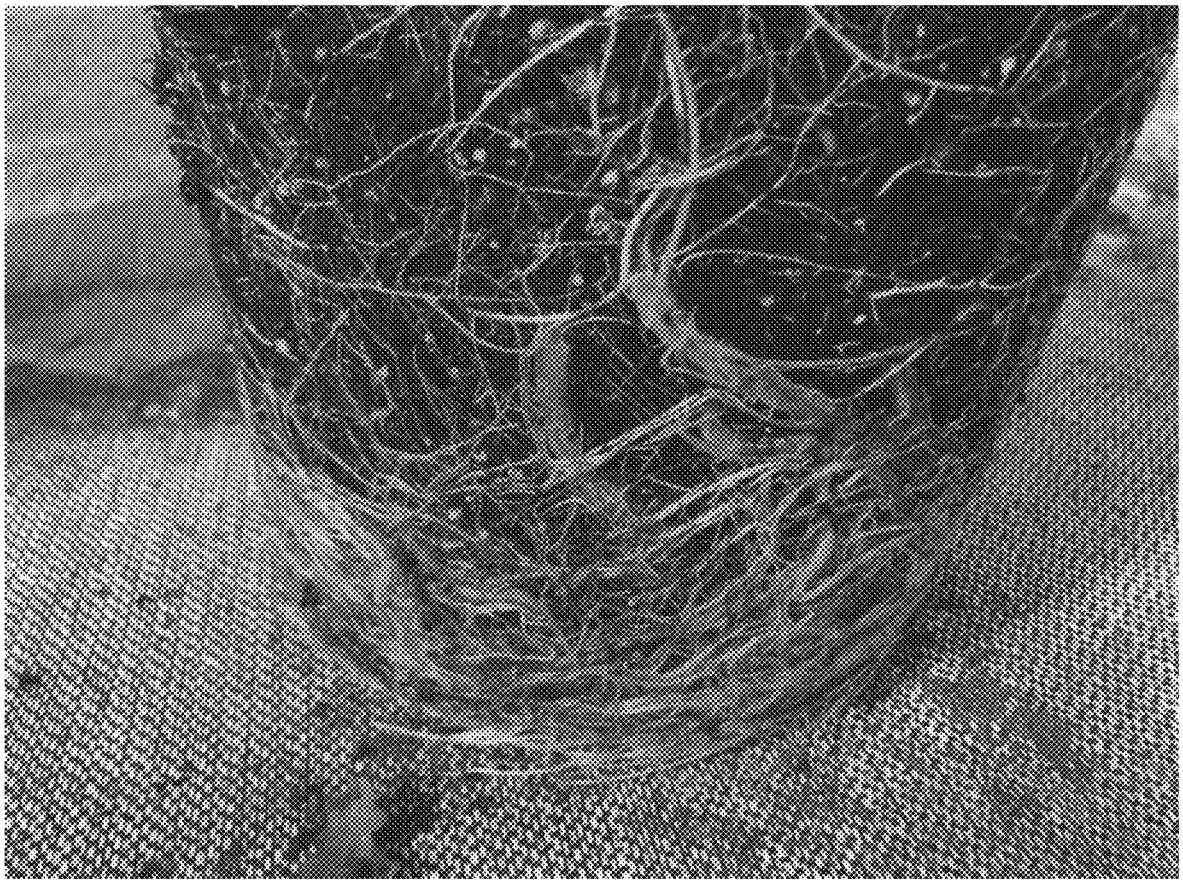
FIG. 2 is a photograph of the roots of the new variety 'Jandrie', which was photographed December 2020 of a plant growing under a cold plastic tunnel.
Figure 3:
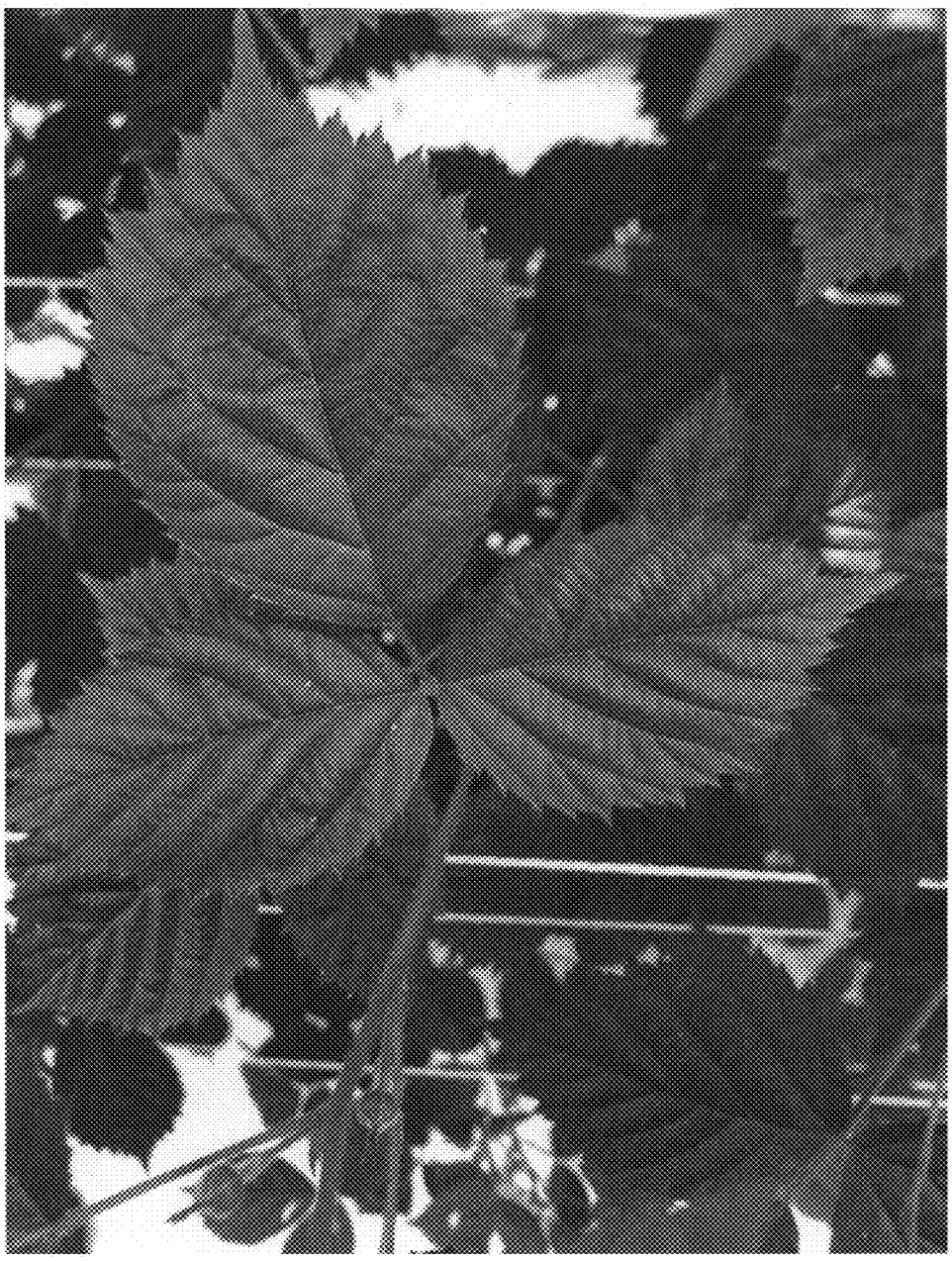
FIG. 3 is a photograph of the foliage of the new variety 'Jandrie', which was photographed on Mar. 7, 2021.
Figure 4:
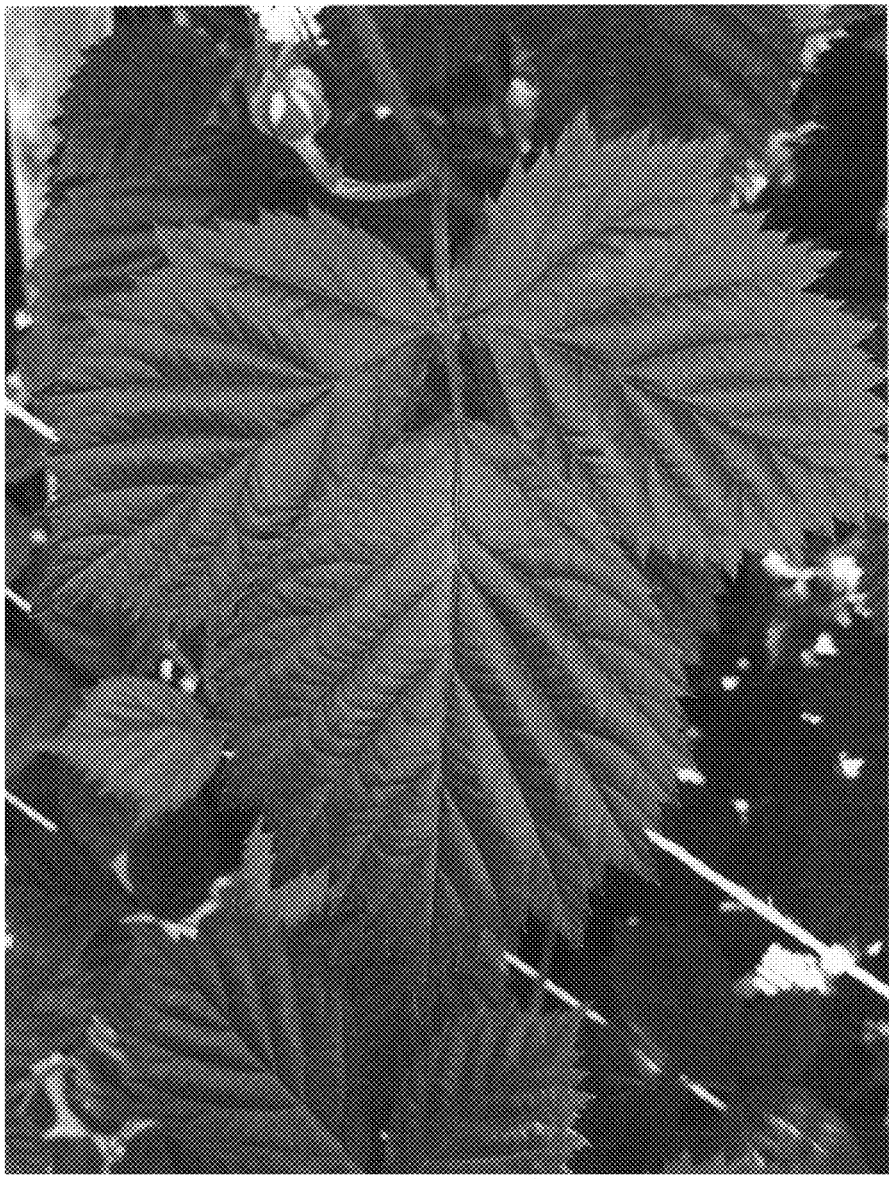
FIG. 4 is a photograph of the foliage of the new variety 'Jandrie' and displays a flower bud and was photographed Mar. 7, 2021.
Figure 5:
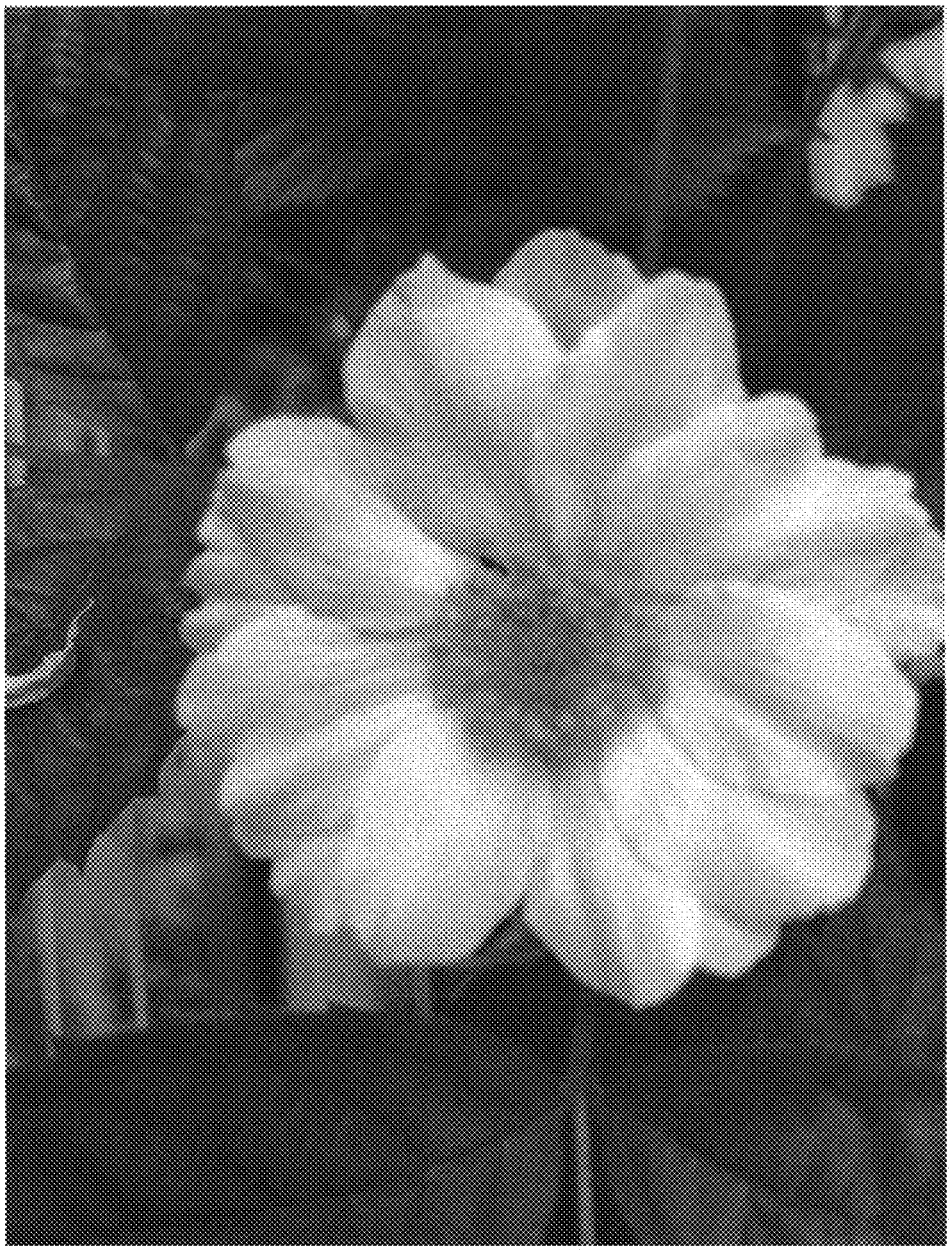
FIG. 5 is a photograph of an early bloomed flower of the new variety 'Jandrie', which was photographed on Mar. 7, 2021.
Figure 6:
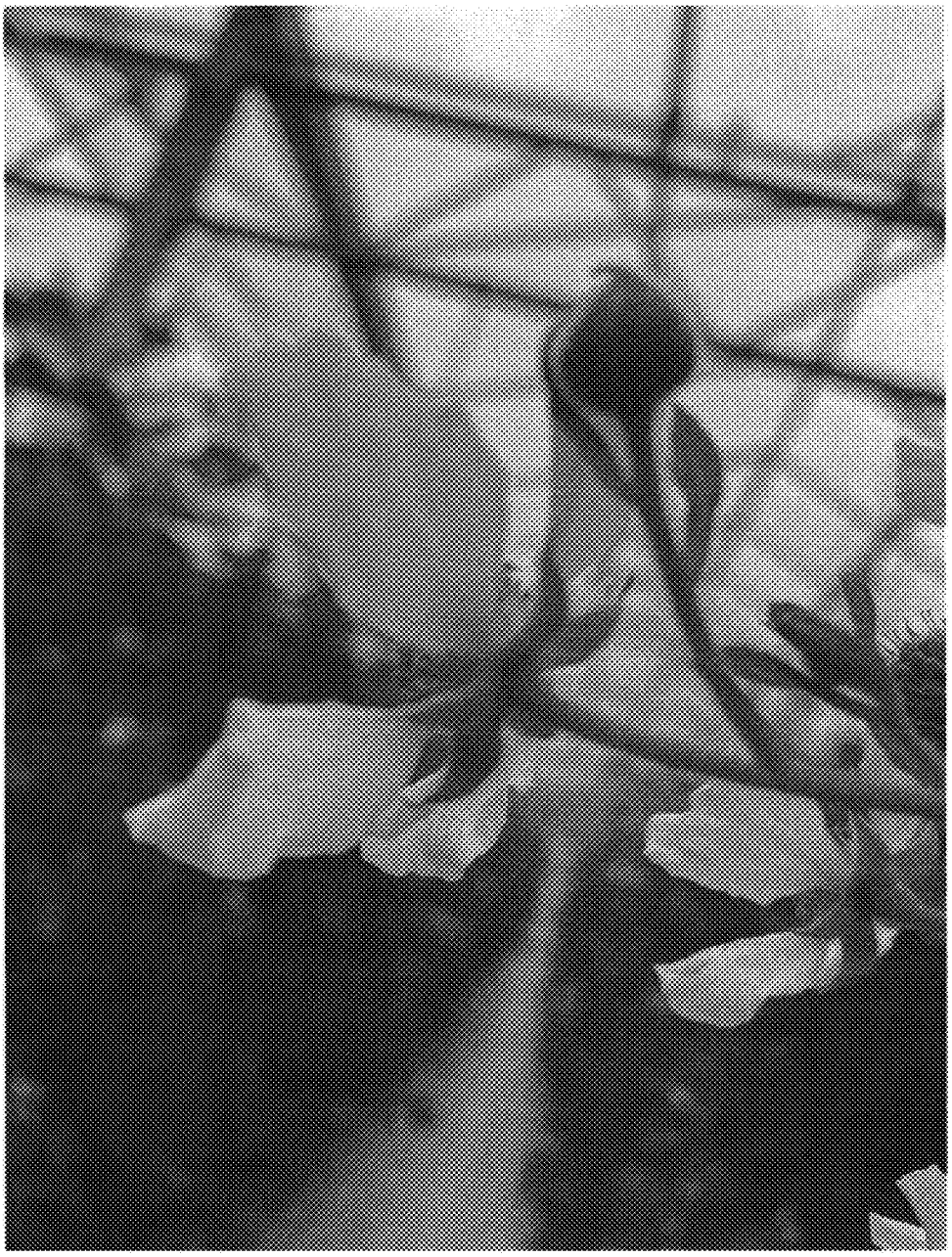
FIG. 6 is a photograph of older flowers of the new variety 'Jandrie', which was photographed on Apr. 2, 2021.
Figure 7:
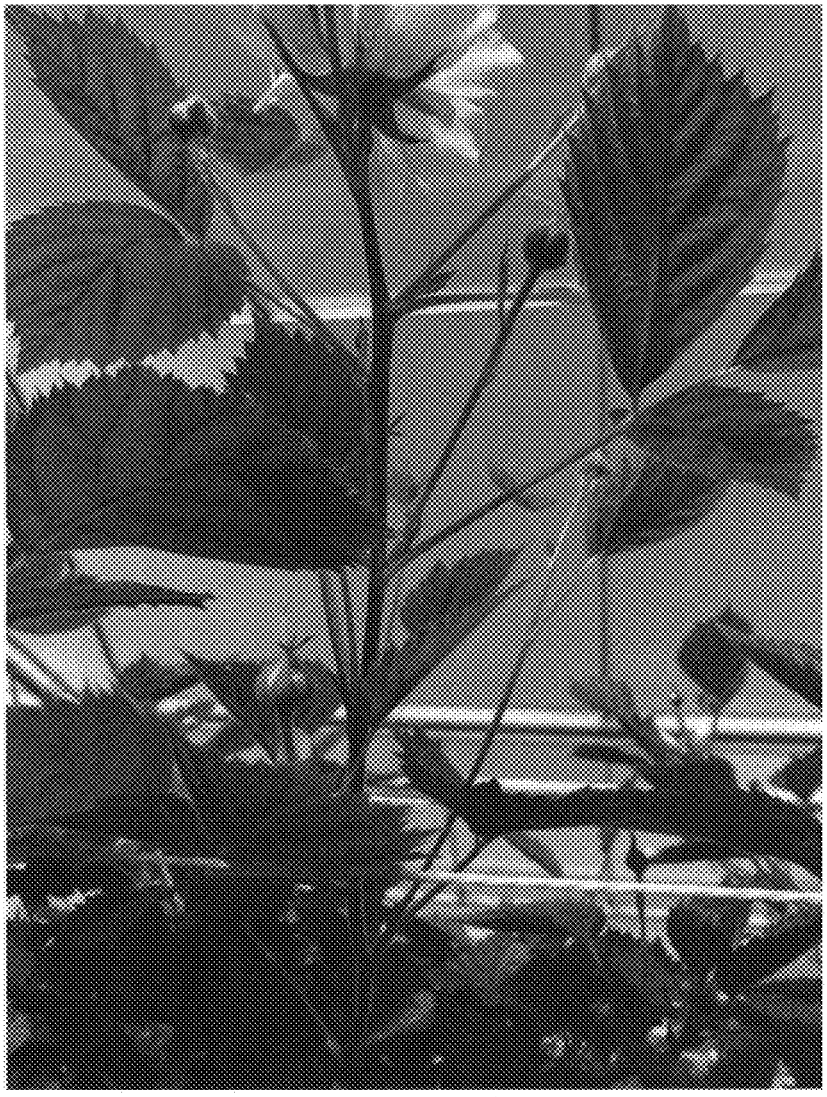
FIG. 7 is a photograph of a cane of the new variety 'Jandrie' displaying leaves and inflorescence, which was photographed on Mar. 7, 2021.
Figure 8:
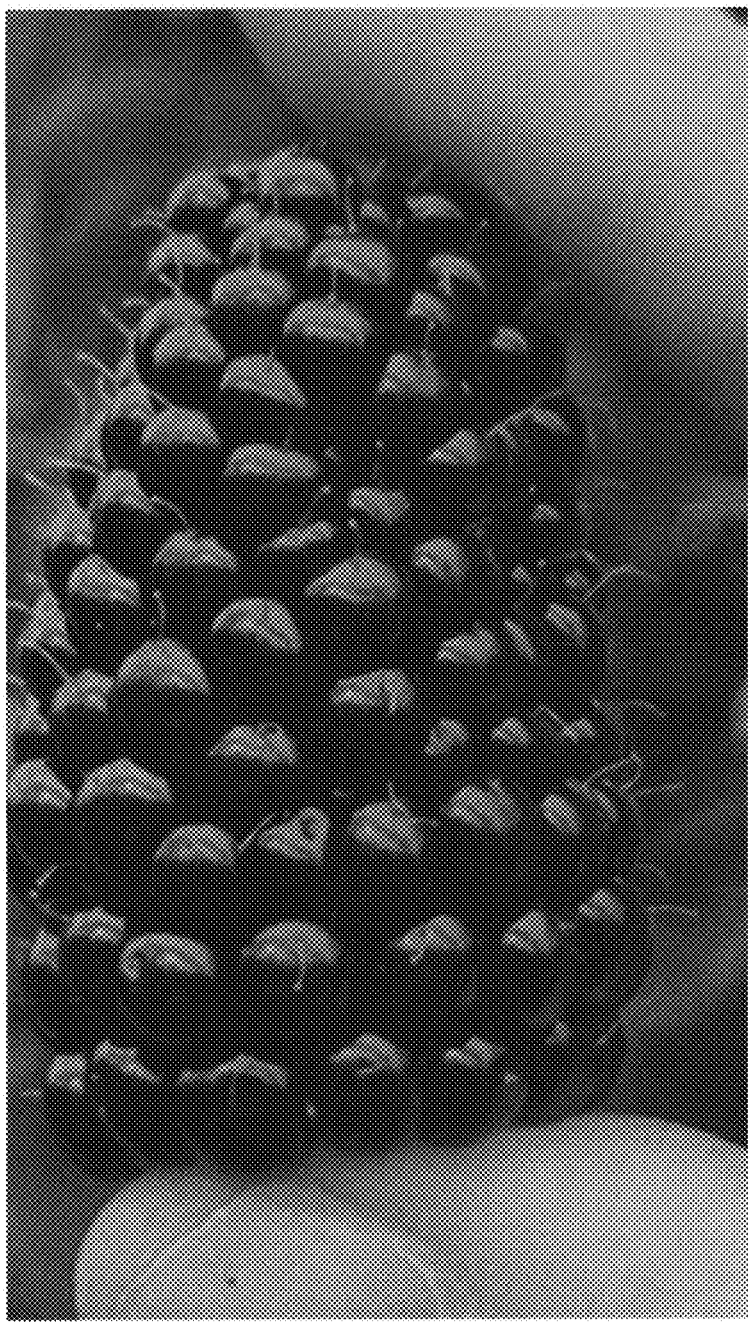
FIG. 8 is a photograph of a mature fruit of the new variety 'Jandrie', which was photographed May 2020.
Figure 9:
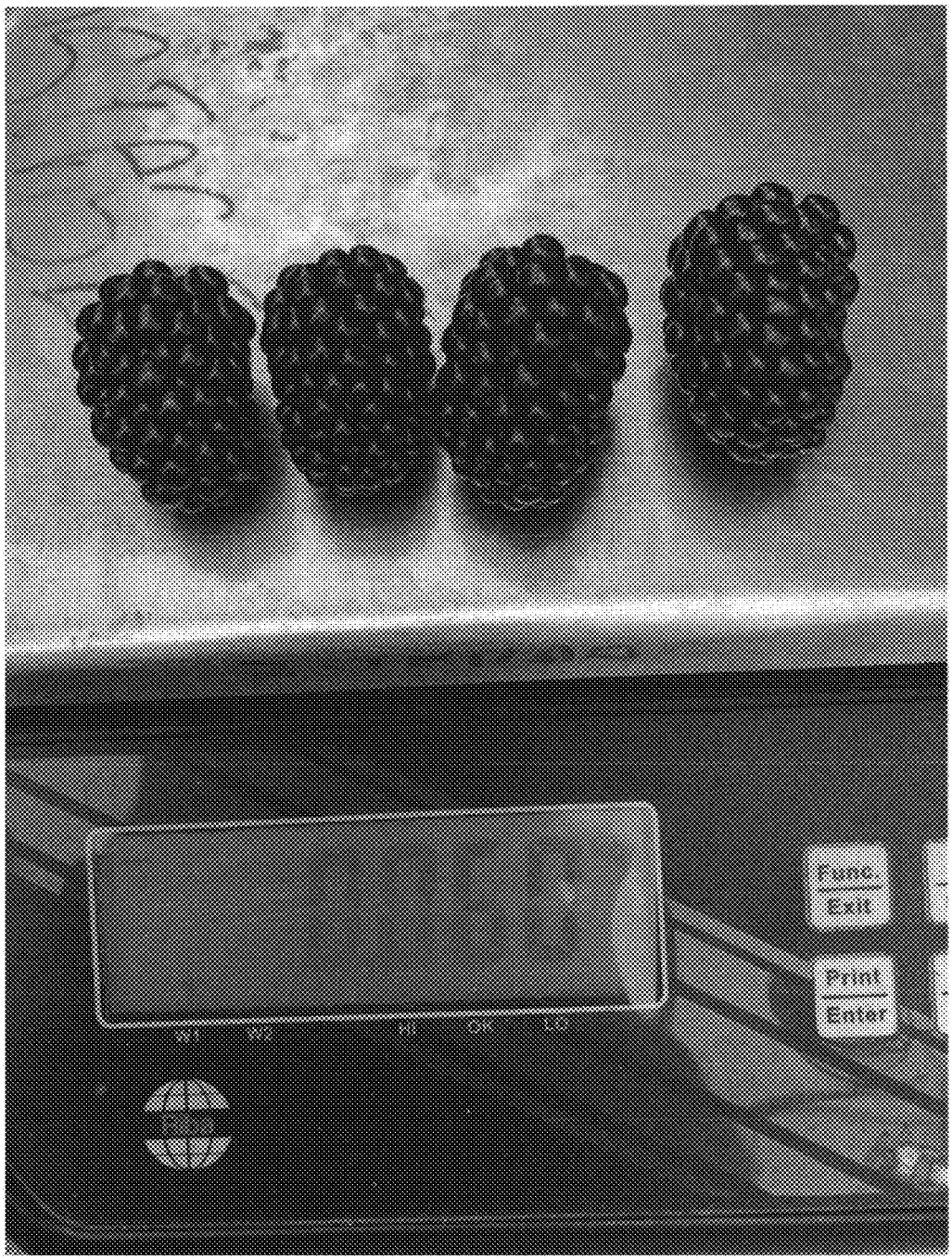
FIG. 9 is a photograph of mature fruits of the new variety 'Jandrie' on a scale, which was photographed May 2020.
Figure 10:
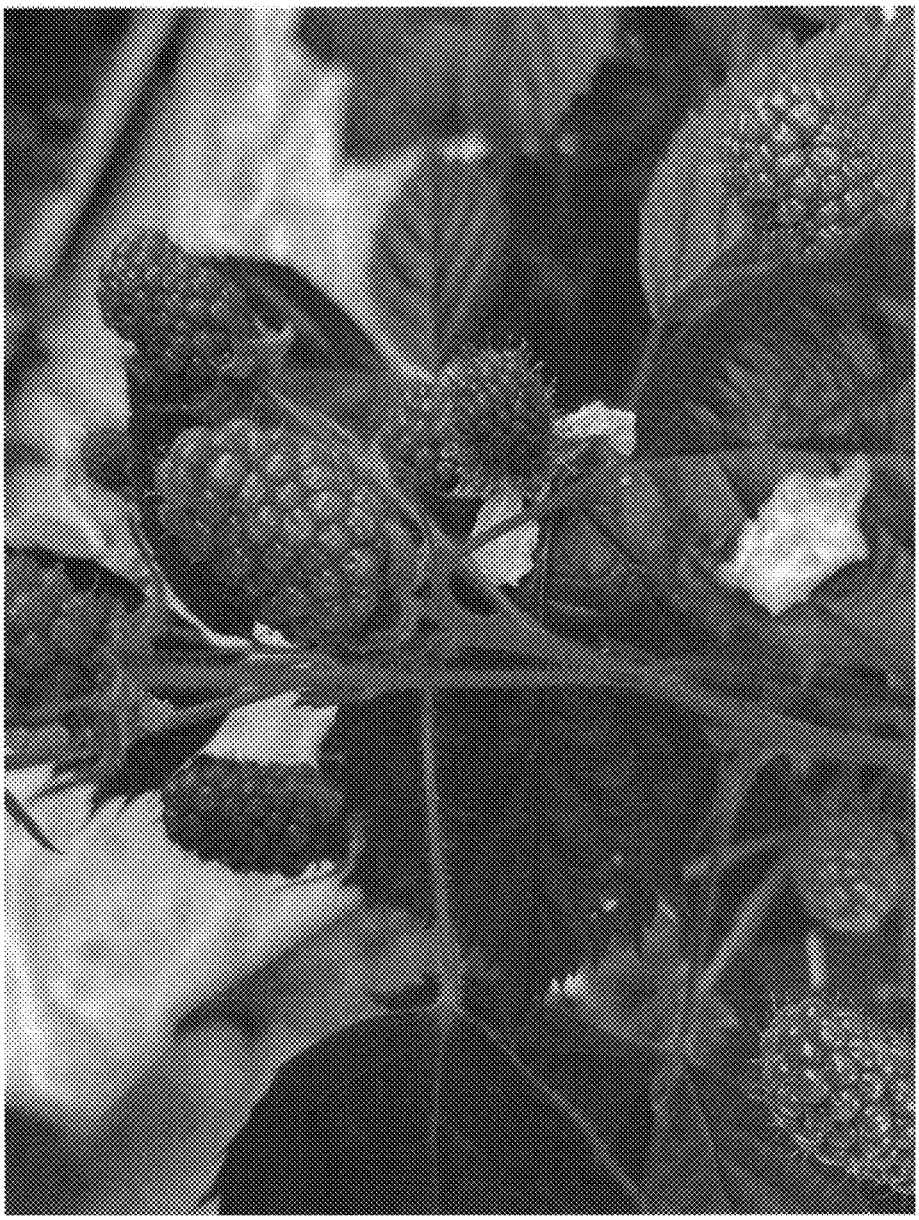
FIG. 10 is a photograph of the immature fruit cluster of the new variety 'Jandrie', which was photographed on Apr. 5, 2021.
Figure 11:
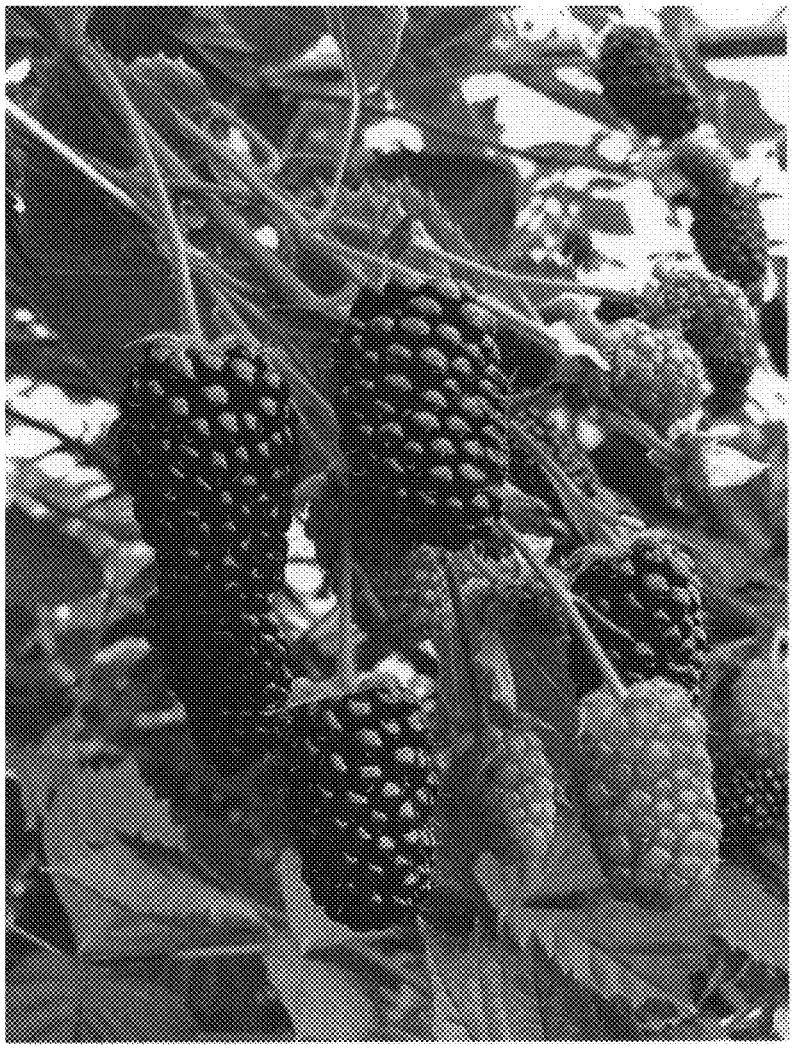
FIG. 11 is a photograph of the mature fruit cluster of the new variety 'Jandrie', which was photographed May 2020.

The following detailed description sets forth the distinctive characteristics of 'Jandrie'. The data which defines these characteristics was collected from asexual reproductions of the original selection. Dimensions, sizes, colors, and other characteristics are approximations and averages set forth as accurately as possible. The chart used in the identification of the colors is that "The Pantone Book of Color" (by Leatrice Eiseman and Lawrence Herbery, Harry N. Abrams, Inc., Publishers, New York 1990). The terminology which precedes reference to the chart has been added to indicate the corresponding color in more common terms. The following descriptions of 'Jandrie' are based on observations of two-years-old specimens of the new variety growing in a substrate in 10 Liter pots in a greenhouse in Kinrooi, Belgium. The greenhouse maintains a minimum temperature of 16° C. during the day, or 20° C. under sunny conditions, and 8° C. during the night. The substrate contained perlite, cocos and peat and a slow-release fertilizer and micronutrients. Water with nutrients was provided with a drip irrigation system in each of the pots.

Classification:

*Family*.—Rosaceae.

*Botanical*.—*Rubus* L. *Rubus*.

*Common name*.—Blackberry.

*Variety name*.—'Jandrie'.

Parentage:

*Female parent*.—Unknown.

*Male parent*.—Unknown.

Plant:

*Growth habit*.—Upright to semi-upright.

*Number of new canes*.—Medium.

*Guttation*.—Strong, i.e., high root pressure.

*Roots*.—A number of the roots are light brown and thick, having the thickness of a pencil. At the outside of the root ball there are a lot of small, white hair roots.

*Productivity*.—Very high, 65 to 75 tons/ha under optimum growing conditions.

*Propagation*.—Tissue culture, stem cuttings, and root cuttings.

*Time of bud burst*.—Very early.

*Fertilizer requirement*.—Requires more magnesium than other varieties due to the darker leaf color.

Canes:

*Dormant cane*.—Length: medium. Diameter (in central third): medium. Anthocyanin coloration: absent or very weak, the sunny side is commonly near 7644c and the shade side is commonly near 574cp. Number of branches: few. Predominant distribution of branches: Young plants need to be topped to generate five or six branches/shoots. Cross section: rounded to angular. Spines: absent.

*Cane internodal distance*.—Relatively small compared to 'Loch Ness' (U.S. Plant Pat. No. 6,782), on average: 8.5 cm.

*Young shoots*.—Anthocyanin coloration (during rapid growth): medium commonly near 209c. Intensity of green color: dark, commonly near 575c. Number of glandular hairs: absent or few (few on the lateral branches, absent on the main cane).

*Spines*.—Absent.

*Fruiting lateral length* ($4^{th}$ *lateral from tip*).—Short to medium, on average 46 cm, color is commonly near 574cp.

*Number of flowers/fruits per fruiting lateral*.—Usually 8 to 10, but at the top of the plant usually 10 to 14.

*Fruiting on current year's cane*.—Absent.

Leaves:

*Type*.—Palmate.

*Predominant number of leaflets*.—Three.

*Intensity of green color of upper side*.—Dark, commonly near 7736cp.

*Color of lower surface*.—commonly near 4214cp.

*Glossiness of upper side*.—Strong.

*Nerves*.—The middle leaf vein is light yellow commonly near 2289c, the other veins are green.

*Leaflet*.—Type of incision of margin: bi-serrated. Depth of incisions: medium to deep.

*Terminal leaflet*.—Length: short, on average 9 cm. Width: narrow to medium, on average 7 cm. Length/width ratio: 1.3. Lobing: absent. Shape in cross-section: V-shaped. Undulation of margin: absent or very weak. Blistering between veins: strong.

*Lateral leaflet*.—Length: on average 8 cm. Width: on average 4 cm. Length/width ratio: 2.0.

*Petiole*.—Size of stipules: large. Length: 15 mm, Width: 5 mm; Color: commonly near 4216c.

*Rachis length between terminal leaflet and adjacent lateral leaflet*.—On average 15 mm.

*Rachis and petiole*.—Covered with a lot of small hairs.

Inflorescence:

*Time of beginning of flowering on previous year's cane*.—Very early.

*Flower*.—Diameter: large, on average 50 mm.

*Petals*.—Number: first developing flowers have three whorls of up to nine petals, later in the flowering season, the flowers have less petals, often only five petals.

*Transition petals*.—Stamens: sometimes, but not always, in the first large developing flowers, there are two small, slightly curled leaves (small curled petals) at the transition between petals and stamens; color is commonly near 454cp.

*Flower*.—Color of petal: white, commonly near 1cp. Color of the anthers (tips of the stamens): light grey.

*Flower number (at 3rd node from tip of lateral)*.—On average 1.

*Flower bud*.—Diameter just before opening: large, on average 9.5 mm.

*Pedicel*.—Length: on average 45 mm. Diameter: on average 1.5 mm.

*Bracteoles*.—Most of the pedicels have one or more small leaves, bracteoles, on the pedicel underneath the flower; color is commonly near 4216c.

Fruit:

*Time of beginning of fruit ripening on previous year's cane*.—Very early.

*Harvest interval*.—In heated greenhouse: as from about April 14 until July 10 (when the top of the canes are bent downwards mid-February to generate new fruiting laterals at the basis of the old fruiting laterals), in high cold plastic tunnels: as from the end of May (May 25th) until the end of August.

*Fruit color*.—Immature: commonly near 576cp: Maturing: commonly near 7608cp; Mature: commonly near 6c.

*Glossiness*.—Glossy.

*Fruit length*.—Long to very long, up to 40 to 45 mm and even longer.

*Fruit width*.—Broad, up to 30 mm or even thicker.

*Ratio of length to width*.—Large, about 1.6.

*Weight (g/fruit)*.—On average 12 g, but fruit can grow up to 17 to 18 g.

*Taste*.—Very sweet, due to the low acidity.

*Fruit*.—Number of drupelets: many to very many, up to about 80 to 100.

*Fruit*.—Size of drupelets: large.

*Fruit stem*.—Covered with a lot of small hairs.

*Fruit*.—Shape in longitudinal section: long conical.

*Flesh of the fruit*.—Color: purple to black.

*Fruit*.—Firm fruits, easy to pick, rigid outside, soft inside, do substantially not leak.

*Yield*.—High, up to 65 to 75 tons/ha under optimal conditions. Fruiting laterals start producing fruit more quickly from the top to the bottom of the plant, hence a high production capacity is quickly obtained after the beginning of the fruit ripening. The fruit production continues moreover for a longer period thus resulting in the high yield.

*Postharvest handling*.—Storability: excellent, can be stored 7 to 8 days in a cold storage room. Can also be stored relatively long on the shelf, with the fruit remaining glossy. Higher resistance to temperature fluctuations, less or nearly no formation of red drupelets.

*Picking intervals*.—Need only to be picked every 5 to 6 days. As a result high fruit picking speeds are possible, about 12 kg/hour.

Disease, pest, and stress resistance:

*Downy mildew*.—No observation of downy mildew on the new variety to date.

COMPARISON WITH COMMERCIAL VARIETIES

Differences with 'Loch Ness' (U.S. Plant Pat. No. 6,782)

Internodal distance of the dormant cane of 'Jandrie' is much shorter than the internodal distance of 'Loch Ness'.

The dormant cane and the leaves of 'Jandrie' have a darker green color than the dormant cane and the leaves of 'Loch Ness'.

The leaves are about 20% smaller than the leaves of 'Loch Ness'.

Start of flowering of 'Jandrie' is about 10 days earlier than 'Loch Ness' and is comparable with 'Loch Tay' (not patented) which is the earliest variety in Belgium.

Flower buds of 'Jandrie' are larger than the flower buds of 'Loch Ness'.

Differences with 'DrisBlackSix' (Victoria™) (U.S. Plant Pat. No. 25,502)

Start of fruit ripening is about 9 to 10 days earlier for 'Jandrie' compared to 'DrisBlackSix'.

Yield is about 65 to 75 tons/ha for 'Jandrie' whereas the yield of 'DrisBlackSix' is, under the same conditions, about 50 to 55 tons/ha.

Picking interval of 'DrisBlackSix' is about 3 days whereas the picking interval of 'Jandrie' is 5 to 6 days.

'DrisBlackSix' is very susceptible to downy mildew whereas downy mildew has not yet been observed on 'Jandrie' by the inventor.

The fruiting laterals of 'Jandrie' are thicker, stronger, and shorter compared to the fruiting laterals of 'DrisBlackSix' which are very long and have to be wound around ropes.

The leaves of 'Jandrie' are darker green than the leaves of 'DrisBlackSix' and are about 18% smaller.

The fruits of 'Jandrie' have more small hairs (remnants of stigmas and styles), have a firmer shell and are much sweeter than the fruits of 'DrisBlackSix'. The small hairs are moreover brown and thick and project outwards, whereas only some of the drupelets of 'DrisBlackSix' have small hairs which are moreover more white and softer and less upright.

The invention claimed is:

1. A new and distinct variety of blackberry plant named 'Jandrie' as described and shown herein.

* * * * *